(12) United States Patent
Stucky et al.

(10) Patent No.: US 7,409,870 B2
(45) Date of Patent: Aug. 12, 2008

(54) ELEVATOR LOAD BEARING MEMBER WEAR AND FAILURE DETECTION

(75) Inventors: Paul A. Stucky, Stockton, CA (US); William A. Veronesi, Hartford, CT (US)

(73) Assignee: Otis Elevator Company, Farmington, CT (US)

( * ) Notice: Subject to any disclaimer, the term of this patent is extended or adjusted under 35 U.S.C. 154(b) by 88 days.

(21) Appl. No.: 10/598,401

(22) PCT Filed: Mar. 16, 2004

(86) PCT No.: PCT/US2004/007899

§ 371 (c)(1),
(2), (4) Date: Aug. 28, 2006

(87) PCT Pub. No.: WO2005/095252

PCT Pub. Date: Oct. 13, 2005

(65) Prior Publication Data
US 2007/0180925 A1    Aug. 9, 2007

(51) Int. Cl.
*G01N 3/32*    (2006.01)
(52) U.S. Cl. ...................................... 73/810
(58) Field of Classification Search ................ 73/810
See application file for complete search history.

(56) References Cited

U.S. PATENT DOCUMENTS

| | | | | |
|---|---|---|---|---|
| 4,266,632 A | * | 5/1981 | Yoneda et al. | 187/382 |
| 4,308,935 A | * | 1/1982 | Deric | 187/248 |
| 4,427,940 A | | 1/1984 | Hirama et al. | |
| 4,650,037 A | * | 3/1987 | Husson et al. | 187/391 |
| 5,058,710 A | * | 10/1991 | Iwasa | 187/290 |
| 5,392,879 A | * | 2/1995 | Boyce et al. | 187/393 |
| 5,402,066 A | | 3/1995 | Hickman, Jr. et al. | |
| 5,731,528 A | | 3/1998 | Yamazaki et al. | |
| 5,757,641 A | * | 5/1998 | Minto | 700/4 |
| 5,881,971 A | * | 3/1999 | Hickman | 244/1 R |
| 6,073,728 A | | 6/2000 | Olsen et al. | |
| 6,163,733 A | * | 12/2000 | Rubel | 700/130 |
| 6,633,159 B1 | | 10/2003 | Robar et al. | |

FOREIGN PATENT DOCUMENTS

DE    39 34 654 A1    5/1991

OTHER PUBLICATIONS

PCT International Search Report for International Application No. PCT/US04/07899, mailed Aug. 27, 2004.
PCT Written Opinion of the International Searching Authority for International Application No. PCT/US04/07899, mailed Aug. 27, 2004.
PCT International Preliminary Report on Patentability for International Application No. PCT/US04/07899, completed May 24, 2005.

* cited by examiner

*Primary Examiner*—Max Noori
(74) *Attorney, Agent, or Firm*—Carlson, Gaskey & Olds

(57) ABSTRACT

An elevator load bearing member (22) monitoring device (20) has a controller (30) that applies a first signal (40) and a second signal (50) to at least one tension member (24) in the belt. The first signal (40) in one example has a plurality of (42) of a selected amplitude and duration. The second signal (50) includes a series of pulses (52) having a second, shorter duration and lower amplitude. The first signal is useful for providing information regarding a wear condition of the load bearing member. The controller utilizes a response to the second signal to determine a failure condition such as a broken load bearing member.

23 Claims, 1 Drawing Sheet

ELEVATOR LOAD BEARING MEMBER WEAR AND FAILURE DETECTION

FIELD OF THE INVENTION

This invention generally relates to monitoring the condition of an elevator load bearing member. More particularly, this invention relates to using different signals for determining a wear condition and a potential failure condition of an elevator load bearing member, respectively.

DESCRIPTION OF THE RELATED ART

Elevator systems typically include a load bearing member such as a rope or belt that bears the weight of the car and counterweight and allows the car to be moved as desired within the hoistway. For many years, steel ropes were used. More recently, coated steel belts or jacketed ropes have been introduced that include a plurality of tension members encased within a jacket. In one example, the tension members are steel cords made up of steel strands. The jacket comprises a polyurethane material.

One difference between the new load bearing members and old steel ropes that presents new challenges is that the jacket covering over the tension members makes visual inspection of the condition of the tension members impossible. Various inspection techniques have been proposed. Some of those techniques are electricity based and rely upon the conductive qualities of the tension members within the belt to make determinations regarding the condition of the tension members.

One device that is useful with the newer types of belts is a broken belt switch, which provides an indication of a broken belt, for example. Such switches are useful for providing an indication of a severe defect or failure condition of a belt. One drawback to mechanical broken belt switches is that they potentially might be engaged or activated because of an unusual mechanical condition even though the elevator belt is fine. It is also possible for such switches to be vandalized. One other issue presented by using a separate broken belt switch is that there is additional hardware, installation and potential maintenance cost. Of course, it is desirable to minimize the complexity associated with elevator systems.

There is a need for an improved technique for monitoring the wear condition of a belt and for determining whether the belt is broken or otherwise severely damaged. This invention provides a unique way of making both types of determinations without relying upon the traditional broken belt switch arrangement.

SUMMARY OF THE INVENTION

In general terms, this invention is an elevator load bearing member monitoring arrangement that uses two different types of signals for making two different types of determinations regarding the condition of the load bearing member.

One example method for monitoring a condition of an elevator belt includes applying a first signal that has a first characteristic to at least one of the tension members in the belt. A second signal that has a second different characteristic is applied to at least one of the tension members in the belt. A wear condition of the belt is determined based upon a response to the first signal. A failure condition of the belt is determined based upon a response to the second signal.

In one example, the resistance of the tension member is determined based upon the applied signals. The information provided by the second signal preferably is continuously monitored so that a broken belt situation can readily be determined. The response to the first signal may be taken over time as normal wear on an elevator belt typically occurs incrementally over long periods of time.

In one example, the first signal characteristic is a first frequency and the second signal has a second, higher frequency.

An example device for monitoring a condition of an elevator belt includes a controller that applies a first signal to at least one of the tension members in the belt. The controller also applies a second signal to at least one of the tension members in the belt. The first signal preferably has a characteristic such as a frequency that is different than a corresponding characteristic of the second signal. The controller utilizes the electrical performance of the tension members in response to the first and second signals to determine a wear condition and a failure condition of the belt, respectively.

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
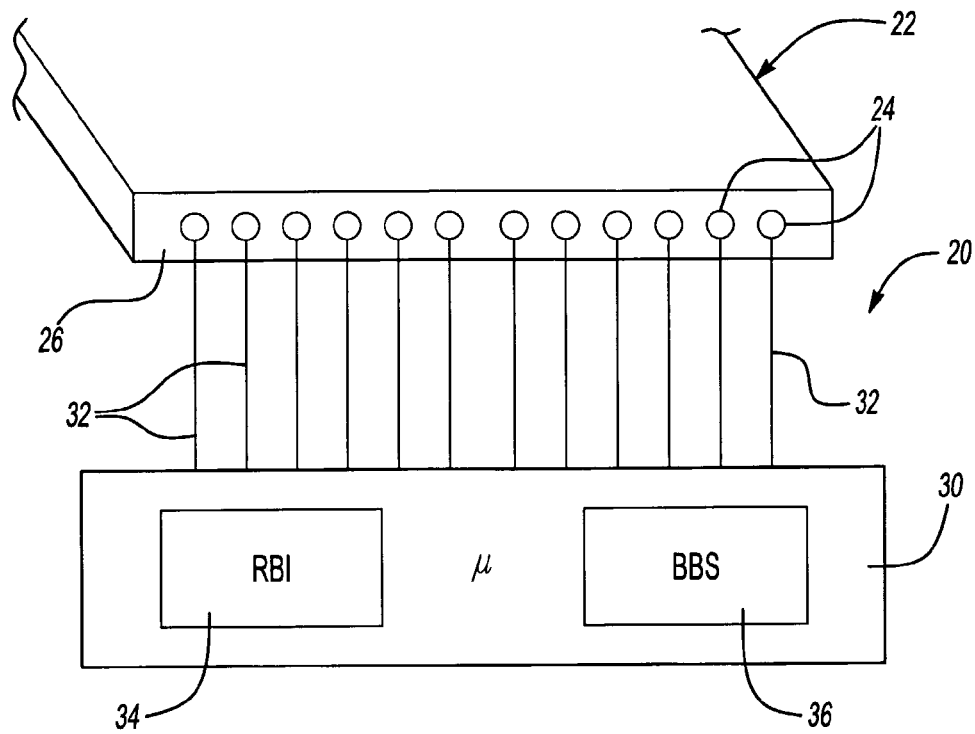
FIG. 1 schematically illustrates an elevator belt assembly including a device designed according to an embodiment of this invention for monitoring a wear condition and a failure condition of the belt.

FIG. 1 schematically shows an elevator load bearing member assembly including a monitoring device 20 and an elevator belt 22. While a belt is shown in this example, the invention is not limited to a specific kind of load bearing member. A plurality of tension members 24 are encased in a jacket coating 26. In one example, the tension members 24 comprise steel cords made up of individual steel strands wound in a conventional manner. The jacket coating 26 in one example comprises a polyurethane material. The tension members 24 carry the loads of the elevator system associated with the car and counterweight and provide the ability to move the car as desired within the hoistway in a conventional manner.

The monitoring device 20 includes a controller 30 that selectively applies electrical signals to the tension members 24. Electrical couplings with the tension members 24 are schematically illustrated at 32. Although FIG. 1 illustrates an electrical connection between each tension member 24 and the controller 30, it may be possible to utilize the techniques provided by this invention by monitoring one or only a selected number of the tension members 24. In one example, multiple tension members 24 are electrically coupled for monitoring purposes.

The controller 30 includes a first module 34 that is designed to enable the controller 30 to monitor the normal wear on the belt 22 during the service life of the belt within the elevator system. In one example, resistance based inspection (RBI) is used where a resistance value of the tension members 24 provides an indication of the mechanical integrity of the tension members. It is known, for example, that a damaged or frayed wire has a higher resistance than one with uninterrupted mechanical integrity. Those skilled in the art who have the benefit of this description will be able to select an appropriate monitoring technique (i.e., which variables to monitor and how to relate them to the condition of the tension members) to suit the needs of their particular situation.

The controller 30 uses the first module 34 to apply a first type of signal to at least one of the tension members 24 to make a determination regarding the wear condition of the belt assembly 22. A second module 36 enables the controller 30 to make a determination regarding a severe failure or broken condition of the belt 22. The second module 36 may replace a separate, mechanical broken belt switch or provide a supplemental indication in systems that include a broken belt switch. The second module 36 allows the controller 30 to apply a second type of signal to the tension members 24 to make a separate determination regarding a failure condition of the belt 22. The second module 36 allows the controller 30 to make an instantaneous check for tension member continuity along the entire length of the belt 22, even along portions of the belt that would not be "visible" to another type of inspection system.

In one example, the first module 34 and the second module 36 comprise software programming on a microprocessor, which serves as at least part of the controller 30. In another example, the first and second modules 34 comprise hardware or firmware. In yet another example, a combination of software, hardware and firmware provides the functionality of the illustrated modules.

Figure 2:
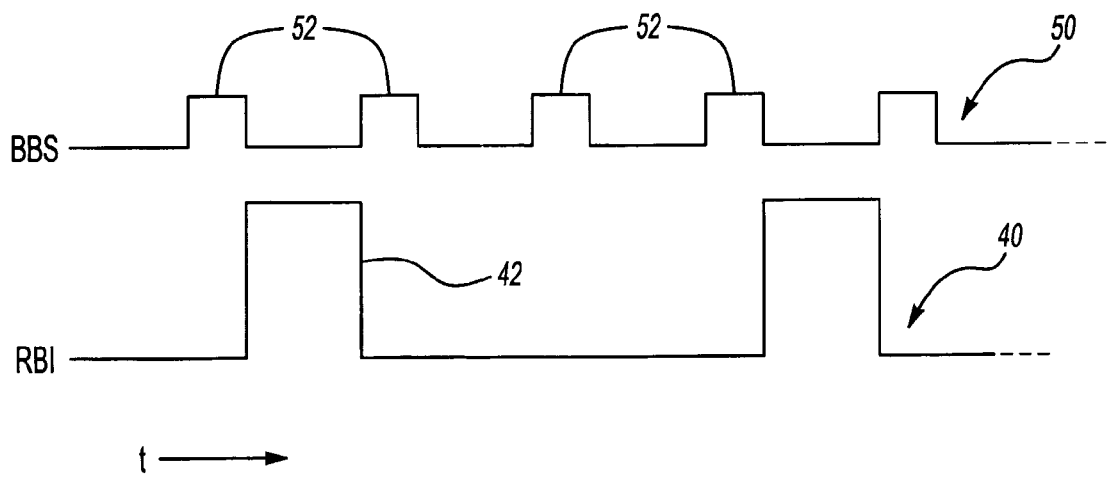
FIG. 2 is a timing diagram schematically illustrating example signals used with the embodiment of FIG. 1.

FIG. 2 schematically illustrates two example signals applied by the controller 30 to make the two different types of belt condition determinations. A first signal trace is shown at 40, which represents a first signal applied by the controller 30 using the first module 34. The signal 40 includes a plurality of pulses 42 having a selected duration and amplitude.

The frequency of the first signal 40 is relatively low compared to that of a second signal 50 shown in FIG. 2. The second signal 50 is applied by the controller 30 to at least one of the tension members 24 as directed by programming within the second module 36, in one example. The second signal 50 includes a plurality of pulses 52 that have a shorter duration and lower amplitude compared to the pulses 42 of the first signal 40. The frequency of the second signal 50 is much higher than that of the first signal 40. The second signal 50 allows the controller 30 to make a broken belt or failure condition determination while the first signal 40 allows the controller 30 to make a wear condition determination.

The higher frequency, lower amplitude and shorter pulse duration of the second signal 50 allows the controller to continuously and instantaneously monitor whether the belt 22 is broken or in a significant failing condition. Using a lower current for the second signal 50 enhances the ability of the system to monitor the belt while not increasing the possibility for accelerating corrosion of the cords (i.e., the tension members) 24 because of the presence of voltages applied to the cords. In one example, the use of a second signal 50 allows for longer intervals between pulses of the first signal 40, which reduces potential corrosion.

A higher frequency for the second signal 50 is preferred because it is important to be able to make instantaneous determinations regarding whether a belt is broken or otherwise in a failing condition. Because the determination of a broken tension member essentially only requires determining electrical continuity along the tension member, the lower amplitude pulses 52 provide sufficient information to make a broken belt determination.

The normal wear that is observable using the first signal 40 is based upon the rate of change in an electrical characteristic of the tension members 24. Electrical resistance of the steel cords of the tension members 24 is used in one embodiment.

Such belts are believed to have a very long service life under normal mechanical and environmental operating conditions. There is a low likelihood of fatigue and wear except over long periods of time. Accordingly, the low frequency of the first signal 40 provides enough information over time to make a determination regarding the wear condition of the belt (i.e., eventual increase in resistance because of eventual wear in the tension members 24). The larger pulses 42 provide more accurate information regarding actual resistance values, which can be integrated over a long period of time to make slight wear determinations.

This invention takes advantage of the difference between the small percentage changes in an electrical characteristic such as resistance of tension members over lengthy periods of time (i.e., 10 to 20 years) and the instantaneous, infinite change in resistance when a tension member 24 becomes broken. These disparate changes allow for the disparate functions to be performed by the single controller 30 using two different types of signals for making the two different types of belt condition determinations.

In one example, the controller 30 and the modules 34 and 36 are programmed so that the signals 40 and 50 are synchronized to avoid any interference between them for the determinations to be made by the controller. In the example of FIG. 2, the pulses 42 are not applied to any of the tension members at the same time that the pulses 52 are applied. The pulses 42 are on during an off time of the pulses 52.

In one example, the controller 30 utilizes a check on a failure condition determination by requiring that a determination of a broken tension member be verified by determining that at least one other tension member in the belt is broken before the controller 30 determines that there is a failure condition of the belt.

In another example, the controller 30 is programmed to determine when the elevator system is in use. During periods of higher use, the controller 30 in this example increases the frequency of the second signal 50 to make a more continuous failure condition inspection. In situations where it is desired to isolate the first signal from the second signal, the first signal frequency may also be adjusted along with adjusting the characteristics of the pulses 42 to fit within the off times of the first signal 50.

In another example, the controller 30 is programmed to increase the monitoring provided by the second signal 50 whenever the results of the wear detection indicate a condition of wear in one or more of the tension members 24. Increased wear may correspond to an increase possibility for a failure condition and the controller in this example adjusts the failure detection accordingly.

Those skilled in the art who have the benefit of this description will be able to select from among commercially available microprocessors and electronics or to custom design software, hardware, firmware or a combination of these to realize the functions provided by the controller of this description. It should be noted that although a single controller 30 with two different modules is schematically illustrated in FIG. 1, individual components may provide the wear condition and the failure condition monitoring.

An inspection device designed according to this invention provides dual functionality, which enhances the economies associated with monitoring the condition of an elevator belt. The inventive arrangement allows for greater sophistication and flexibility compared to mechanical broken belt switches, for example. There is a cost savings associated with eliminating a broken belt switch.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A method of monitoring a condition of a load bearing member in an elevator system, comprising the steps of:
    applying a first signal having a first characteristic to at least one tension member in the load bearing member;
    applying a second signal having a second, different characteristic to at least one tension member in the load bearing member;
    determining a wear condition of the load bearing member based upon a response to the first signal; and
    determining a failure condition of the load bearing member based upon a response to the second signal.

2. The method of claim 1, wherein the first and second characteristics are a frequency and the second frequency is higher than the first frequency.

3. The method of claim 2, wherein the first signal has a first amplitude and the second signal has a second, lower amplitude.

4. The method of claim 2, wherein the first signal comprises a series of pulses having a first duration and the second signal comprises a series of pulses having a second, shorter duration.

5. The method of claim 2, including determining a use condition of the elevator system and increasing the second frequency during periods of higher use.

6. The method of claim 2, including increasing the second frequency if the response to the first signal indicates an increased wear condition.

7. The method of claim 1, wherein the signals each comprise a series of pulses and including synchronizing the signals such that the first signal pulses are not on at the same time as the second signal pulses.

8. The method of claim 1, including determining that a failure condition of the load bearing member exists only when a selected number of tension members provide a response to the second signal indicative of failure.

9. The method of claim 1, including applying the first and second signals, respectively, to a plurality of tension members and determining an individual response of each of the tension members to the signals.

10. The method of claim 1, including periodically determining the wear condition by monitoring the response to the first signal over an extended time and determining the failure condition by continuously monitoring the response to the second signal.

11. A device for monitoring a condition of a load bearing member in an elevator system, comprising:
    a controller that applies a first signal having a first characteristic to at least one tension member in the load bearing member and applies a second signal having a second, different characteristic to at least one tension member in the load bearing member, the controller determines a wear condition of the load bearing member based upon a response to the first signal and determines a failure condition of the load bearing member based upon a response to the second signal.

12. The device of claim 11, wherein the signals each comprise a series of pulses and the controller synchronizes the signals such that the first signal pulses are not on at the same time as the second signal pulses.

13. The device of claim 11, wherein the first signal comprises a series of pulses having a first duration and the second signal comprises a series of pulses having a second, shorter duration.

14. The device of claim 11, wherein the first characteristic is a first frequency and the second characteristic is a second, higher frequency.

15. The device of claim 14, wherein the first signal has a first amplitude and the second signal has a second, lower amplitude.

16. The device of claim 14, wherein the controller determines a use condition of the elevator system and increases the second frequency when the elevator system use exceeds a selected threshold.

17. The device of claim 14, wherein the controller increases the second frequency if the response to the first signal indicates an increased wear condition.

18. The device of claim 11, wherein the controller integrates the response to the first signal over time to make the wear condition determination and continuously monitors the response to the second signal to instantaneously make the failure condition determination.

19. An elevator load bearing member assembly, comprising:
    a plurality of electrically conductive tension members;
    a non-conductive coating over the tension members; and
    a controller electrically coupled with at least one of the tension members, the controller applying a first signal having a first characteristic to at least one tension member in the load bearing member and applying a second signal having a second, different characteristic to the tension member, the controller determining a wear condition of the load bearing member based upon a response to the first signal and determining a failure condition of the load bearing member based upon a response to the second signal.

20. The assembly of claim 19, wherein the first characteristic is a first frequency and the second characteristic is a second, higher frequency.

21. The assembly of claim 19, wherein the first signal and the second signal are electrical signals.

22. The device of claim 11, wherein the first signal and the second signal are electrical signals.

23. The method of claim 1, wherein the first signal is an electrical signal and the second signal is an electrical signal.

* * * * *